(12) United States Patent
Saad (10) Patent No.: US 9,877,743 B2
(45) Date of Patent: Jan. 30, 2018

(54) CIRCULAR SURGICAL SCALPEL AND MARKER

(71) Applicant: Natural Nipple Knife LLC, Philadelphia, PA (US)

(72) Inventor: Adam Saad Ahmed Saad, Northfield, NJ (US)

(73) Assignee: Natural Nipple Knife LLC, Philadelphia, PA (US)

( * ) Notice: Subject to any disclaimer, the term of this patent is extended or adjusted under 35 U.S.C. 154(b) by 101 days.

(21) Appl. No.: 14/157,264

(22) Filed: Jan. 16, 2014

(65) Prior Publication Data
US 2014/0200602 A1   Jul. 17, 2014

Related U.S. Application Data

(60) Provisional application No. 61/753,745, filed on Jan. 17, 2013.

(51) Int. Cl.
*A61B 17/32* (2006.01)
*A61B 17/3211* (2006.01)
*A61B 90/00* (2016.01)

(52) U.S. Cl.
CPC .......... *A61B 17/3211* (2013.01); *A61B 90/39* (2016.02); *A61B 2090/395* (2016.02); *A61B 2090/3908* (2016.02); *A61B 2090/3937* (2016.02)

(58) Field of Classification Search
CPC ................ A61B 17/3211; A61B 90/39; A61B 2090/3908
See application file for complete search history.

(56) References Cited

U.S. PATENT DOCUMENTS

| | | | | | |
|---|---|---|---|---|---|
| 4,791,928 A | * | 12/1988 | Berke | ........... | A61B 17/32 30/319 |
| 4,873,991 A | * | 10/1989 | Skinner | ........... | A61B 10/0266 30/113.1 |
| 5,035,703 A | * | 7/1991 | Baskas | ........... | A61M 5/3213 604/192 |
| 5,569,237 A | * | 10/1996 | Beckenstein | ....... | A61B 90/39 604/116 |
| 5,578,054 A | * | 11/1996 | Arnold | ........... | A61F 2/10 606/167 |
| 5,676,161 A | * | 10/1997 | Breiner | ........... | A61B 17/32053 128/898 |
| 5,795,308 A | * | 8/1998 | Russin | ........... | A61B 10/0266 600/567 |
| 5,824,076 A | * | 10/1998 | Knowlton | ........... | A61F 2/12 128/898 |
| 2002/0045858 A1 | * | 4/2002 | Alchas | ........... | A61M 5/3129 604/117 |

(Continued)

*Primary Examiner* — Richard Louis
(74) *Attorney, Agent, or Firm* — Keith D. Nowak; Carter Ledyard & Milburn LLP (57) ABSTRACT

Disclosed herein are devices useful for marking and making circular incisions in surgeries particularly breast surgeries. The devices generally comprise a body, a central handle and a marking or cutting implement affixed to one end. Also disclosed herein are kits comprising the marking and/or cutting implements and methods for improving breast surgeries comprising using a device for circularly marking and making the surgical incisions. The devices and methods can provide improved cosmetic results and improved healing.

6 Claims, 4 Drawing Sheets

(56) References Cited

U.S. PATENT DOCUMENTS

| | | | |
|---|---|---|---|
| 2004/0236315 A1* | 11/2004 | Hered | A61B 90/39 606/1 |
| 2005/0149092 A1* | 7/2005 | Dunn | A61B 10/02 606/185 |
| 2005/0187512 A1* | 8/2005 | Isola | A61B 17/320068 604/22 |
| 2005/0261603 A1* | 11/2005 | Wittenberg | A61B 10/02 600/566 |
| 2005/0267506 A1* | 12/2005 | Harris | A61B 17/32053 606/187 |
| 2006/0167338 A1* | 7/2006 | Shfaram | A61B 17/0401 600/37 |
| 2007/0239067 A1* | 10/2007 | Hibner | A61B 10/0096 600/567 |
| 2007/0261174 A1* | 11/2007 | Barker | B26B 5/00 7/160 |
| 2007/0265491 A1* | 11/2007 | Krag | A61B 17/32053 600/37 |
| 2008/0065129 A1* | 3/2008 | Batchelor | A61B 18/1485 606/172 |
| 2008/0275481 A1* | 11/2008 | Scarpone | A61B 17/3421 606/172 |
| 2009/0253981 A1* | 10/2009 | Hamilton | A61M 35/006 600/414 |
| 2009/0256981 A1* | 10/2009 | Yang | G09G 3/3648 349/40 |
| 2014/0074118 A1* | 3/2014 | Esarey | A61B 17/322 606/132 |

* cited by examiner

CIRCULAR SURGICAL SCALPEL AND MARKER

CROSS-REFERENCE TO RELATED APPLICATIONS

This claims benefit of U.S. Provisional Patent Application No. 61/753,745, filed Jan. 17, 2013, the entirety of which is incorporated herein by reference.

BACKGROUND

Field of the Invention

This relates generally to methods for making surgical incisions using scalpels and related surgical devices. More particularly this relates to devices and methods that facilitate improved surgeries, such as breast surgeries, and specifically, the incisions involved therein.

Description of Related Art

For a variety of reasons including the prevalence of breast disease and the practical or other basis for cosmetic or corrective operations, breast surgeries have increased in number. For example, in 2011, patients underwent almost 100,000 breast reconstruction surgeries, more than 63,000 breast reduction surgeries, and over 90,000 mastopexies. In addition to these large numbers of surgeries, other breast-related surgeries were performed, including areolar reduction surgeries, the number of which is not easily ascertained.

One aspect that most if not all of these surgeries share is the need for circular incisions, for example to move the nipple and related tissue(s) and/or to provide for optimal healing and cosmetic results. Given the relative prevalence of such surgeries, common practices have become fairly standard. Typically a surgeon makes two substantially circular incisions. Ideally these incisions would be perfectly circular. However, drawing a perfect circle by hand is difficult if not impossible even for a gifted artist. Cutting a perfect circle with a standard scalpel, under the conditions present during the course of surgery is even more challenging. The surgeon works on an uneven surface, i.e. the patient, and must make his circular incision on areas having varying surface properties, firmness, density, and consistency, in addition to other properties that affect how a particular tissue or region of tissue will respond to the surgeon's efforts.

In the case of breast surgeries, these circular incisions can serve to preserve the blood supply to the patient's nipple as well as to facilitate the future placement of the nipple.

During breast reductions or mastopexies, a first circular incision is made as follows: methylene blue ink is brushed onto an areolotome, e.g. with a cotton swab. The areolotome is then used to mark a circular path around the patient's nipple. The diameter of the circular path corresponds to the desired size of the new nipple. The areolotome is then removed and a standard scalpel is used to cut along the marked path.

After the initial incision, the nipple and its underlying tissue/blood supply is freed from the enveloping skin. Any excess skin and/or breast tissue is removed and the nipple is repositioned. The remaining skin is draped over the nipple. A second circular incision allows the nipple to come through the breast skin in its new position. The areolotome is again brushed with methylene blue ink. It is then placed on overlying breast skin above the nipple in order to mark the new position of the nipple. Finally, the areolotome is removed and a standard scalpel blade is used to cut along the circular marked path. The skin within the marking is discarded and the nipple is brought through the hole into its new position. It is then sutured to the surrounding skin.

These incisions are extremely important, as the circular nipple area that has been incised and remains intact forms the patient's post-surgery nipple, which is placed in the circular area of the second incision. The accuracy and precision of the circularity and matching of these two circular incisions are of utmost importance to the final post-operative healing and appearance of the breast and the nipple. Any imperfections, deviations, or errors in these incisions can lead in the worst cases to improper or delayed healing, scarring, or deformity of the patient's nipple and breast (including risk of nipple twisting or loss of the nipple), or in the best case only to a less desirable aesthetic result of the breast surgery.

There is a need for alternative and improved methods to make these incisions.

SUMMARY

Devices to improve a surgeon's ability to make one or more circular incisions during a surgical procedure are provided herein. Also provided are methods of using the devices for surgical procedures.

In a first aspect, this disclosure provides marking devices comprising a body having a central integral handle portion adapted for convenient handling by a surgeon during surgery. The marking devices also comprise a marking implement, preferably adapted for making a temporary circular mark on a subject, wherein the marking implement is affixed to one end of the body. The marking implement extends or protrudes sufficiently from the end of the device body to allow the marking of the subject with the marking implement while avoiding substantial contact between the subject and the device body.

In a second aspect, surgical cutting devices are provided. Like the marking devices, the surgical devices generally comprise a body having a central integral handle portion adapted for handling by a surgeon during surgery. The devices further comprise a cutting implement adapted for making a circular incision on a subject. The cutting implement is affixed to one end of the body and extends or protrudes sufficiently from the end of the device body to allow making an incision of the desired depth on the subject while avoiding substantial interfering contact between the subject and the device body.

A third aspect of the disclosure provides surgical devices which combine features of the first two aspects herein. Surgical devices for marking the proper location for a surgical incision on a patient and subsequently making said incision is provided. The devices generally comprise a body having a central handle portion adapted for handling by a surgeon during surgery, a marking implement adapted for making a temporary circular mark on the patient, and a cutting implement adapted for making a circular incision on the patient. The marking implement is affixed to a first end of the body and extends or protrudes sufficiently from the first end of the device body to allow making an incision of the desired depth on the subject while avoiding substantial contact between the subject and the device body. The cutting implement is affixed to a second end of the body and extends or protrudes sufficiently from the end of the device body to allow making an incision of the desired depth on the subject while avoiding substantial interfering contact between the subject and the device body. In certain embodiments, the device comprises an incision depth restriction means for use in connection with the cutting implement to aid the surgeon by limiting or restricting the depth of the incision.

Another aspect of this disclosure provides methods of making a surgical incision comprising the steps of:
- a) providing a marking device comprising a body having a central handle portion adapted for handling by a surgeon during surgery, and a marking implement adapted for making a temporary circular mark on a patient, wherein the marking implement is affixed to a first end of the body and extends or protrudes sufficiently from the end of the device body to allow the marking of the patient with the marking implement while avoiding substantial contact between the patient and the device body; wherein the marking implement comprises a circular marker;
- b) using the marking device for making a circular mark on the patient in at least a first location on the patient's body where a circular incision is desired;
- c) providing a surgical cutting device comprising a body having a central handle portion adapted for handling by a surgeon during surgery, and a cutting implement adapted for making a circular incision on a subject, wherein the cutting implement is affixed to a first end of the body and extends or protrudes sufficiently from the end of the device body to allow making an incision of the desired depth on the subject while avoiding substantial interfering contact between the subject and the device body, wherein the cutting implement comprises a circular scalpel; and
- d) using the cutting device to make a circular incision on the patient in at least the first location.

Another aspect of the disclosure provides kits comprising together in a single package, or in separate packages:
- a) one or more of:
  1) a marking device comprising a body having a central handle portion adapted for handling by a surgeon during surgery, and a marking implement adapted for making a temporary circular mark on a patient, wherein the marking implement is affixed to a first end of the body and extends or protrudes sufficiently from the end of the device body to allow the marking of the patient with the marking implement while avoiding substantial contact between the patient and the device body;
  2) a surgical cutting device comprising a body having a central handle portion adapted for handling by a surgeon during surgery, and a cutting implement adapted for making a circular incision on a subject, wherein the cutting implement is affixed to a first end of the body and extends or protrudes sufficiently from the end of the device body to allow making an incision of the desired depth on the subject while avoiding substantial interfering contact between the subject and the device body, wherein the cutting implement comprises a circular scalpel; and
  3) a combination marking and cutting device comprising a body having a central handle portion adapted for handling by a surgeon during surgery, and at least first and second ends wherein the first end has affixed thereto a marking implement adapted for making a temporary circular mark on a patient, wherein the marking implement extends or protrudes sufficiently from the first end of the device body to allow the marking of the patient with the marking implement while avoiding substantial contact between the patient and the device body, and wherein the second end has affixed thereto a cutting implement adapted for making a circular incision on a subject, wherein the cutting implement extends or protrudes sufficiently from the end of the device body to allow making a circular incision of the desired depth on the subject while avoiding substantial contact between the subject and the device body, wherein the cutting implement comprises a circular scalpel; and
- b) any one or more of instructions for use; written, video, or audio information on using the components of the kit, breast surgery, cosmetic surgery or making circular incisions during surgery, or how a surgeon or hospital can benefit from the kit; information about improving cosmetic results of a breast surgery, a label or other indicia that encourages or promotes use of the devices or the kit for improved cosmetic results in surgeries, or a label or other indicia indicating the devices contained therein are single-use or conditions under which they may be reused; or a link (in the form of a URL) to a website that comprises information on any of the foregoing.

These and/or further aspects, features, and advantages of the present invention will become apparent to those skilled in the art in view of this disclosure.

DETAILED DESCRIPTION

Provided herein are marking devices, surgical cutting devices and methods for improving surgeries, particularly breast surgeries by allowing a surgeon to make perfectly circular or nearly perfectly circular incisions and to align impacted areas or tissues during reconstructive work for optimal cosmetic results.

The inventors have discovered that a simple circular marking implement and a circular cutting implement or circular scalpel disclosed herein unexpectedly provide a substantially improved result over current surgical tools for this purpose, and over current practices in the surgical suite.

Surprisingly, the inventors have also discovered that despite prevalence of breast surgeries, particularly reconstructive surgeries and surgeries for which the cosmetic results are paramount, there are no simplified means of marking a surgical site for a circular incision or for making such an incision accurately. By providing a simple marking device that optionally allows for perfect or nearly perfect circular incisions and perfect or nearly perfect alignment of the tissues during reconstruction, the inventors have offered a solution to this problem that was heretofore unknown. Moreover, by including a simple means for controlling the depth of the incision, the devices provided herein provide a valuable tool for making a truly circular surgical incision of a predetermined depth in a reproducible fashion.

Definitions & Abbreviations

Unless expressly defined otherwise, all technical and scientific terms, terms of art, and acronyms used herein have the meanings commonly understood by one of ordinary skill in the art in the field(s) of the invention, or in the field(s) where the term is used. In accordance with this description, the following abbreviations and definitions apply.

As used herein, the singular form of a word includes the plural, and vice versa, unless the context clearly dictates otherwise. Thus, the references "a", "an", and "the" are generally inclusive of the plurals of the respective terms. For example, reference to "a scalpel" or "an incision" includes a plurality of such "scalpels" or "incisions."

The words "comprise", "comprises", and "comprising" are to be interpreted inclusively rather than exclusively. Likewise the terms "include", "including" and "or" should all be construed to be inclusive, unless such a construction is clearly prohibited from the context. Further, forms of the terms "comprising" or "including" are intended to include embodiments encompassed by the phrases "consisting essentially of" and "consisting of". Similarly, the phrase "consisting essentially of" is intended to include embodiments encompassed by the phrase "consisting of".

Where used herein, ranges are provided in shorthand, so as to avoid having to list and describe each and every value within the range. Any appropriate value within the range can be selected, where appropriate, as the upper value, lower value, or the terminus of the range.

The methods and devices and/or other advances disclosed here are not limited to particular methodology, protocols, and/or structures described herein because, as the skilled artisan will appreciate, they may vary. Further, the terminology used herein is for the purpose of describing particular embodiments only, and is not intended to, and does not, limit the scope of that which is disclosed or claimed.

Although any devices, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent permitted under applicable law. Any discussion of those references is intended merely to summarize the assertions made therein. No admission is made that any such patents, patent applications, publications or references are prior art, or that any portion thereof is either relevant or material to the patentability of what is claimed herein. Applicant specifically reserves the right to challenge the accuracy and pertinence of any assertion that such patents, patent applications, publications, and other references are prior art, or are relevant, and/or material.

As used herein a "breast surgery" refers to any surgical procedure, manipulation, or modification whether for reason of health or for purely cosmetic purposes. Examples of such surgeries include breast reduction (i.e. mammoplasty), breast removal (i.e. mastectomy), breast reconstruction (including e.g., combined mastectomy and reconstruction, mastopexy, and areolar procedures), breast lift and other procedures.

As used herein "interfering contact" means any contact that impedes, frustrates, diminishes, alters, decreases, or obstructs in any way, a surgeon's ability, ease, or comfort during surgery. For example, contact that to any degree blocks, interrupts, redirects, misdirects, or otherwise impinges upon a surgeon in the act of making an incising on a surgical subject may be interfering contact.

Abbreviations

The following abbreviations apply unless indicated otherwise:
g: gram;
in: inch;
kg: kilogram;
cm: centimeter;
mm: millimeter;
URL: Uniform Resource Locator.

DETAILED DESCRIPTION OF ILLUSTRATIVE EMBODIMENTS

In a first of the several aspects of this disclosure, provided herein are marking devices for marking a subject during or prior to surgery. The marking devices generally comprise a body that features a central integral handle portion adapted for handling by a surgeon during surgery. The device further comprises a marking implement adapted for making a temporary circular mark on a subject. The marking implement is preferably affixed to a first end of the body and generally extends or protrudes sufficiently from the end of the device body to allow the marking of the subject with the marking implement while avoiding substantial contact between the subject and the device body.

In various embodiments, a nearly perfect circular mark can be made on the patient or subject by merely contacting the skin with the marking device, and either pressing and turning the device.

Figure 1:
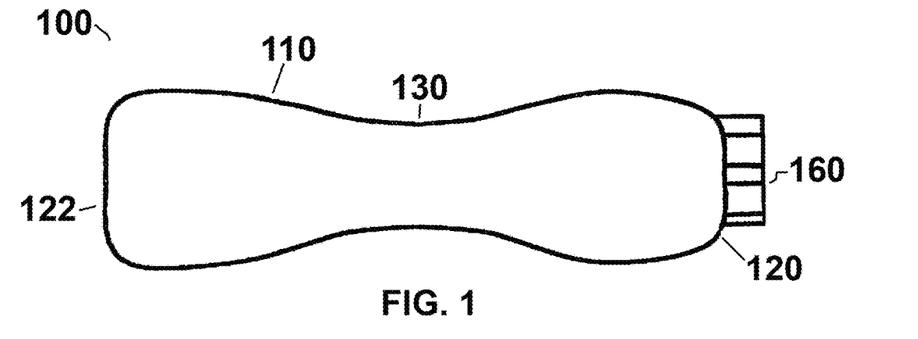
FIG. 1: A depiction of an embodiment of marker device 100 in side view showing the main parts including the body 110, first and second ends 120, 122, a central handle 130, and the marking implement 160.

The device may be better understood with reference to the figures. FIG. 1 depicts an embodiment of a marking device 100 comprising a body 110 and a central handle 130 adapted for convenient handling, or holding by a surgeon during surgery. The body 110 has at least a first end 120 and a second end 122. A marking implement 160 is present on at least the first end 112. The central handle 130 is preferably integral to the body and is adapted for use by a surgeon during surgery.

The central handle 130 is adapted for use by surgeons during surgery. In particular, it is of a weight and of a diameter that will conveniently fit into the hand of a surgeon and which can be manipulated readily under the conditions of surgery without substantial discomfort or fatigue to the surgeon or surgeon's hand. Accordingly, the central handle 130 may be considerably narrower than one or more other portions of the device 100. For example, the device may have an hourglass or dumbbell or similar shape wherein two ends 120, 122 are substantially thicker than the central handle 130 of the body 110. In some embodiments the body 110 may have one end that is enlarged relative to the central handle, while another end is substantially the same diameter as the central handle (not shown). The body 110 may be tapered, or partially tapered, and the central handle 130 may feature burls, surface etchings, depressions, or other structures or other surface modifications that are useful to or designed to facilitate handling, improve grippability, and/or minimize fatigue.

The body 110 and central handle 130 may comprise separate pieces that are assembled together, but preferably the body 110 and handle 130 are manufactured together as a single piece, for example by molding or by milling from a solid piece. The body 110 may be hollow or solid. Any materials may be used for construction of the devices. Preferably the material is sterilizable, for example by steam sterilization, gamma irradiation (e.g. Cobalt-60 exposure), ethylene oxide (EtO), dry heat, electron beam sterilization, or the like. Presently preferred are polymeric materials (e.g. plastics) of various types. Other options include for example, metals (e.g. stainless steel, and a variety of metal alloys), as well as lightweight engineered materials such as ceramics, graphite, nanomaterials, and the like.

The devices disclosed herein may generally be re-usable and resterilizable (e.g. at a hospital or surgical center) or they may be single-use/disposable items that are intended for destruction after use. The skilled artisan will appreciate that the materials selected for various parts or portions may vary depending on whether the device is intended for single- or multi-use. In certain embodiments a portion of the devices (e.g., the body) may be re-usable while a different portion (e.g., the marking implement) may be single-use. In such embodiments, the single-use portion may come pre-sterilized from the manufacturer.

In a presently preferred embodiment, in use the marking implement 160 can be pressed lightly (e.g. "stamped") on the skin of the patient or subject.

The core function of the marking implement 160 is to enable the surgeon to make a mark on the surgical subject or patient prior to making an incision. In preferred embodiments the marking implement 160 comprises a circular marker 180.

Figure 7:
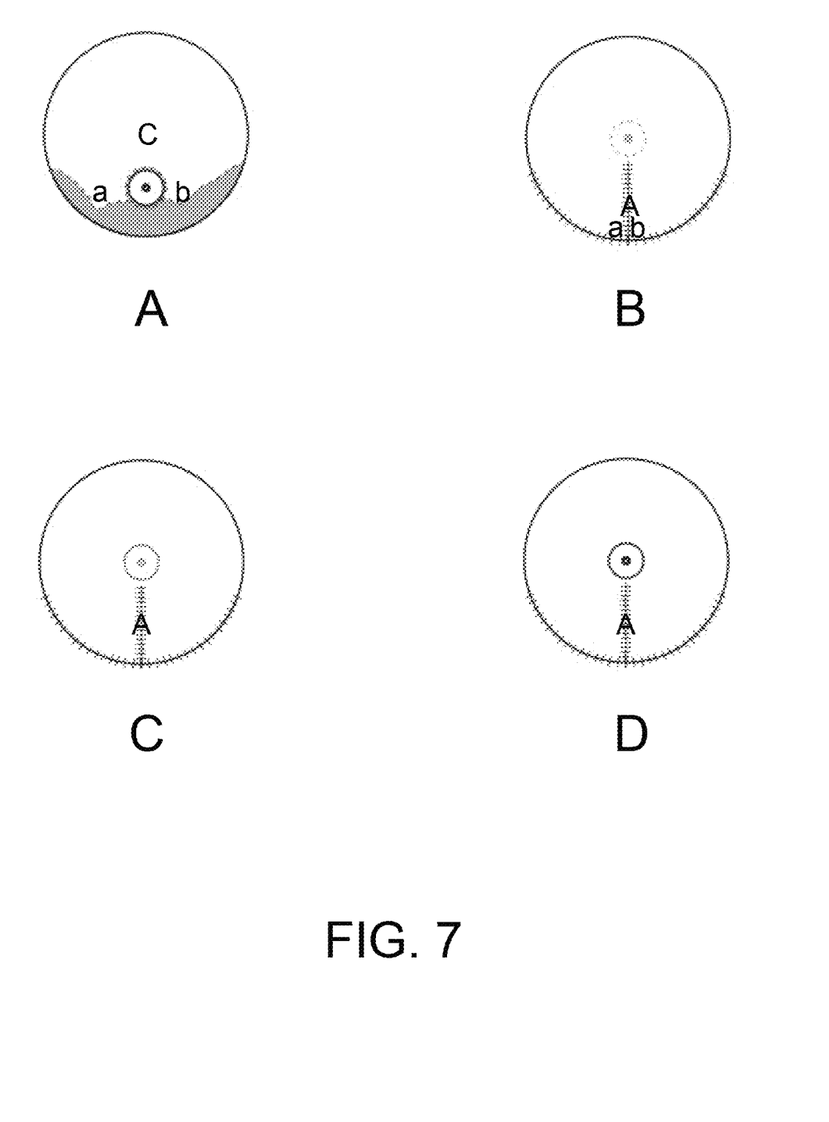
FIG. 7: Depicts a representative surgical sequence showing steps of a procedure (e.g. a breast lift) during which a nipple is relocated from its original location A to a final location C. Panel A: A nipple at location A is marked and a first incision is made with the surrounding tissue cut to the desired depth. The undesired or excess skin (shown as shaded area) may be fully removed. The nipple itself remains attached including its blood supply and innervation; Panel B: The skin from nearby points a and b are brought in adjacent one to the other while the nipple remains below. Points a and b may be connected/attached by suitable means such as (micro)suturing while the nipple is relocated to position C; Panel C: A second incision is marked and cut at position C to form a hole through which the nipple below may be brought; Panel D: The relocated nipple is brought through the hole at location C and sutured into place. Alignment markings present on the nipple and at position C may be present and used to align the nipple so that it is positioned in a similar or identical orientation to that at location A.

In one embodiment, the marking implement 160 creates a circular mark on the subject with one or more additional marks (alignment marks) to allow at least temporary alignment or orientation of the mark during a surgical procedure. In practice this means that one or more of the alignment marks will preferably appear and remain visible in two places: (a) on the incised or excised part of the patient's or subject's body, and (b) the remaining part of the patients' body. In a preferred embodiment, this allows the surgeon to make e.g. a circular incision at a first location, remove surrounding tissue while maintaining the bulk of the vascular and nerve connections intact in the cut area. The surgeon can subsequently close up the site and make a second circular incision at a different location in which he/she can relocate the partially excised (but still connected) tissues from the first incision and reattach that tissue in substantially the original orientation using the alignment marks. In this way the surgeon can assure the original or desired alignment is substantially re-established at the new location. This is exemplified in FIG. 7 showing a nipple being relocated, for example during a breast lift. The end result can provide not only improved cosmetic appearance but also improved conditions for healing and reduced risk of complications.

Figure 2:
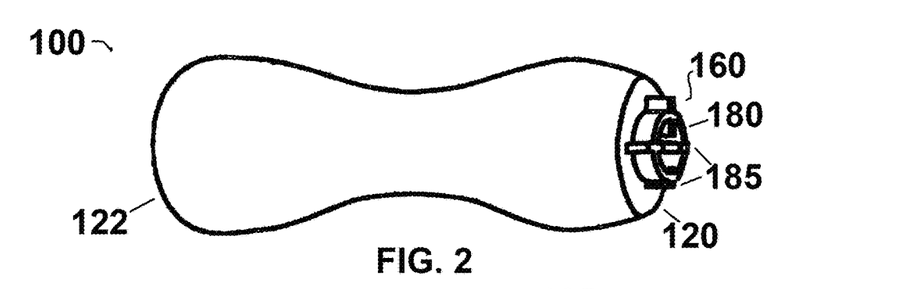
FIG. 2: A view of an embodiment of the marker device 100 showing a partial side view and partial end view. The marking implement 160, circular marker 180, and alignment markers 185 can be seen. In the embodiment shown, the end 120 has a circular shape which is preferred for certain embodiments herein, however the end 120 may in fact have any convenient or useful shape and will not alter the utility of the marker 180 or the alignment markers 185.

This aspect can be seen in the partial side view of the device 100 shown in FIG. 2. The body 110 and central handle 130 are visible with a more complete view of the end 120 with the marking implement 160 affixed thereto. The circular marker 180 is shown. The additional or alignment marks are made via one or more alignment marker portions 185.

Figure 3:
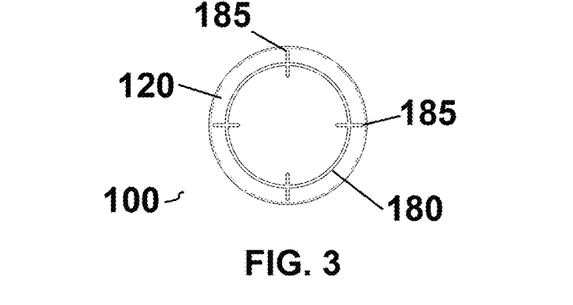
FIG. 3: A profile view of the end 120 of device 100 showing the circular marker 180 and the distribution of the additional alignment markers 185. As depicted, the alignment markers 185 are distributed about every 90 degrees along the circle of marker 180. Other configurations that provide for alignment during surgery are contemplated for use herein.

As shown in FIG. 3, the alignment marks 185 can be distributed substantially symmetrically around the circular marker 180, e.g. separated by about 90 degrees. In one embodiment (not shown) the alignment marker(s) 185 are asymmetrically distributed along the circular marker 180 to allow the original alignment to be readily re-established. A plurality of such additional marks is preferred in some embodiments to provide multiple points of alignment around the periphery of the partially-excised area prior to reattachment, reconstruction, or the like. The skilled artisan will appreciate that, where a second incision at a second location, and relocation of the tissue is involved, the surgeon will align the marking device in substantially the same orientation at both the first and second sites (see e.g. FIG. 7).

The alignment markings 185 of the marking implement 160 can be adapted to make at least one additional mark that is perpendicular to a tangent of the circular mark. In one embodiment, the alignment markings 185 are of sufficient length and positioned to allow the mark to intersect and cross over the main mark (e.g. circular mark) made by the marking implement 160. At least one additional alignment marker 185 generally has a length of less than about one 1 centimeter and is adapted for making a mark as described above for alignment during a surgical procedure.

In certain embodiments the marking implement is adapted with a plurality of alignment markers 185. In one embodiment, there are alignment markers 185 for making at least four (4) additional marks each of which is perpendicular to a tangent of the circular mark, and extends across both sides of the circle mark (i.e. the interior and the exterior of the circle). Preferably at least three of the alignment markers 185 are separated by angle of up to about 120 degrees along the circular marker 180. The alignment markers 185 are separated by about 90 degrees along the circular marker 180 in certain embodiments.

To provide for optimal marking, it is useful for the marking implement 160 to extend or protrude sufficiently from the first end 120 of the device body 110 to allow a circular mark to be made around a raised area on the subject while minimizing or eliminating contacting the patient with the body 130 of the device 100. This is particularly useful wherein the raised area is a nipple, but can also be used to mark moles, cancerous tissue or areas, skin conditions, or localized necrotic areas or infections for removal. In current practice small areas that are merely to be removed may be cut out with the biopsy punch or similar tool. However, if larger area is to be removed, the marking and cutting devices disclosed herein may be useful. In certain embodiments, a substantial area is removed from a visible or cosmetically sensitive area of the subject's body and skin from a less noticeable area is grafted for an improved cosmetic result. By having the skin graft precisely fit to the removal area, an improved outcome for the subject may be attained.

Preferably the marking implement 160 extends or protrudes less than about 1 cm from the device body 110.

In one embodiment, the marking implement 160 receives a manual application of ink suitable for use on a surgical subject. Any ink that is medically acceptable for use in marking surgical sites or use in such procedures may be used herein, including water-based or other marking inks. In one embodiment, the ink is methylene blue, gentian violet, or the like. Preferably the ink is nontoxic based on testing results under the American Society for Testing and Materials D4236 standard for art material. More preferably the ink is cleared or approved by the FDA for use in Class 1 medical devices, for direct skin use, and/or for use in surgical site markers. Also, preferably the ink is in accordance with the Association for periOperative Nurses (AORN) recommendation for such purposes. In one embodiment, the ink selected and the mark made is temporary and does not last for months or even weeks. However the marks are preferably sufficiently durable or persistent such that it persists long enough for the surgery, including remaining clearly visible after prepping the patient or subject (including prepping with or without scrubbing using povidone-iodine solution, hexachlorophene, chlorhexidine gluconate, isopropyl alcohol, detergents, or the like, including combinations thereof).

In other embodiments, the marking device 100 further comprises a reservoir of ink (not shown) suitable for use on a surgical subject. Preferably such a reservoir is refillable or replaceable by the user or by a nurse or other hospital staff member. Such a reservoir could be a cartridge or similar device that is common with writing or drawing implements, marking devices and the like. They may be sufficient to make several required markings during a surgery, but otherwise disposable after a single procedure.

In various embodiments, the marking device 100 or a reusable portion thereof can be resterilized for additional use(s). Materials suitable for such purposes are known in the art of surgical device manufacture. Preferably the device 100 can be steam sterilized for reuse, such as in an autoclave.

The marking device 100 is a single-use item in other embodiments. In yet other embodiments, the marking device 100 features a portion, such as the body 100, that is reusable while the marking implement is a "single-use" item that is disposed after use in a single surgical procedure.

In one embodiment the diameter of the circular marker 180 is selected based on the diameter of a circular incision required in a surgical procedure.

The surgical procedure is preferably a breast surgery and the diameter of the circular marker 180 is the desired diameter of a nipple portion of the breast. In one presently preferred embodiment, the diameter is between about 35 mm and about 50 mm.

Having the ability to mark different sized markings (e.g. circles) for different patients or subjects is desirable. Accordingly, in certain embodiments, the marking implement 100 can be removably attached to the first end of the body; for example, the marking implement 160 can be snap-fit or twist fit into the end 120 of the body. This configuration will allow the marking device 100 to be equipped with a variety of different marking implements 160 of various sizes or even shapes as the surgeons needs dictate. In yet another embodiment, the marking device 100 has a different marking implement 160 affixed at each of two ends (e.g. 120, 122) wherein each can make a different sized mark or circle. Such embodiments are useful where a majority of applications require a small number of mark sizes.

In another embodiment, the marking device 100 can comprise a rotating turret structure having a plurality of marking implements 160. The turret has a plurality of 'stops' that can be rotated into a position with respect to the body 110 adapted for the surgeon to make a needed mark. Each such stop provides a different size marking implement 160.

Figures 8, 9:
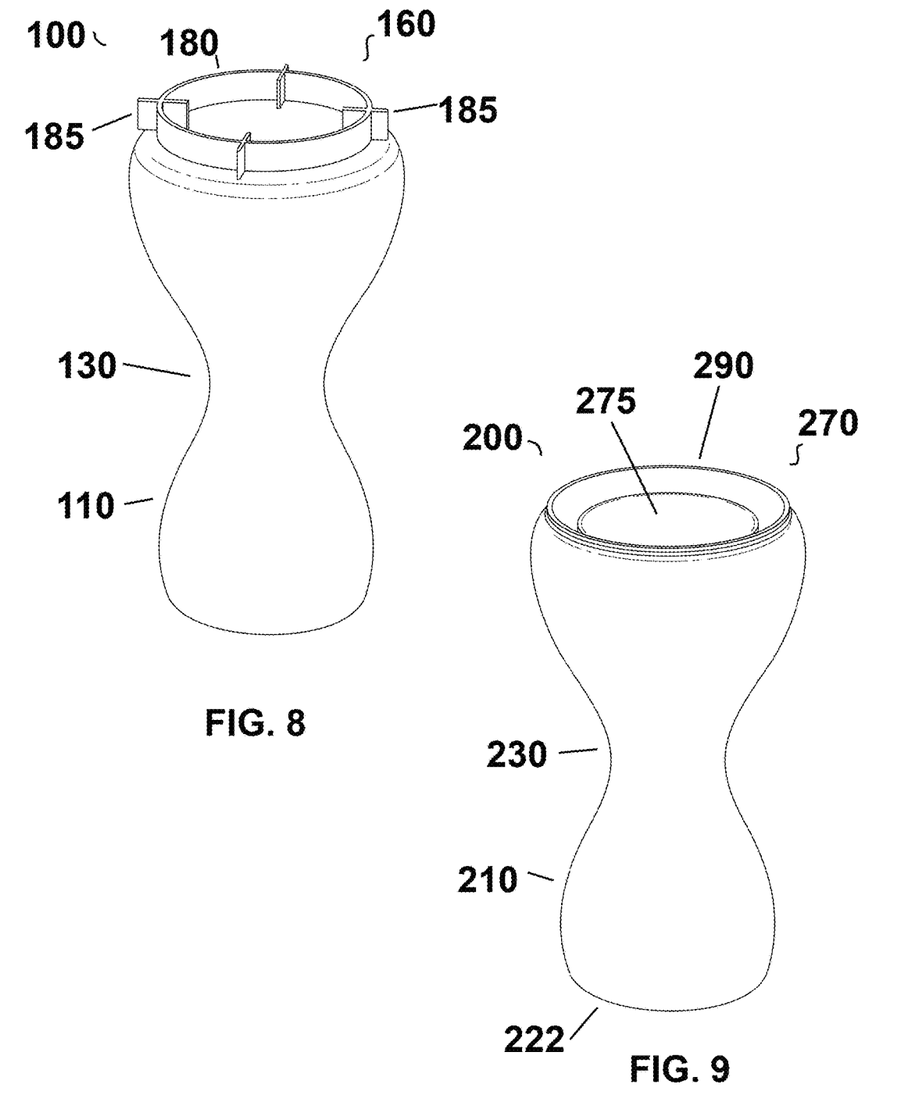
FIG. 8: Depicts an embodiment of the circular marker disclosed herein showing a varied handy and body design.
FIG. 9: Depicts an embodiment of the surgical cutting device further comprising an incision depth stop 275.

It is to be understood that the exact shape of the handle and body of the device may vary. FIG. 8 depicts another embodiment of the marker show a variation of the body and handle.

Another aspect of the invention provides surgical cutting devices. The surgical cutting devices generally a body having a central handle portion adapted for handling by a surgeon during surgery, and a cutting implement adapted for making a circular incision on a subject. The cutting implement is preferably affixed to one end of the body and extends or protrudes sufficiently from the end of the device body to allow making an incision of the desired depth on the subject while avoiding substantial contact between the subject and the device body.

The cutting devices may be constructed substantially similarly to the marking devices described above in the first aspect of the invention.

Figure 4:
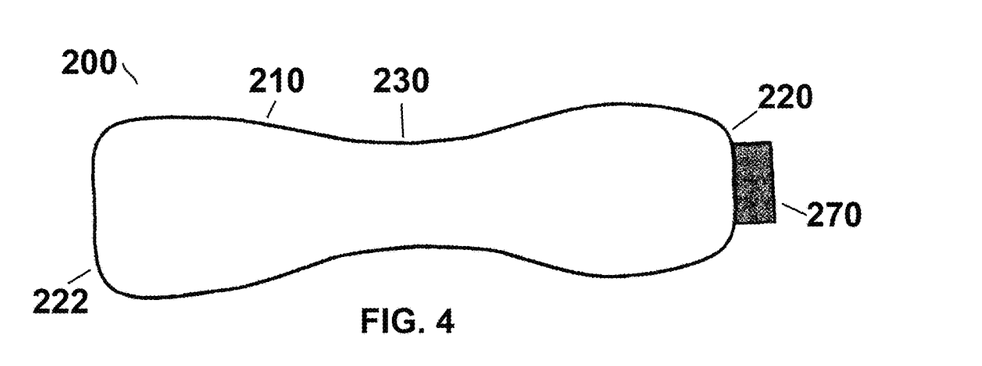
FIG. 4: An embodiment of the surgical cutting device 200 in side-view. The figure depicts device 200 in side view showing the main parts including the body 210, first and second ends 220, 222, a central handle 230, and the cutting implement 270.

With further reference to the figures, FIG. 4 depicts an embodiment of a surgical cutting device 200. The body 210 of the device 200 comprises ends 220, 222 and a central handle portion 230 that is preferably integral to the body 210. The cutting implement 270 is affixed to a first end 220 of the device 200.

In various embodiments nearly perfect circular surgical cut may be made by contacting the area to be surgically cut or removed with the cutting implement 270 (i.e. blade or the like) and then pressing and/or turning the cutting device and applying sufficient pressure to make the surgical incision without cutting too deeply.

It should be noted that the cutting devices disclosed herein are quite different from existing devices. Traditional scalpels are not well-suited to making perfectly circular or nearly perfectly circular incisions. On the other hand, certain tools such as circular punches and similar devices that are used to remove or excise tissues or samples or obtain tissue biopsies are ideally suited for making small circular incisions. However such devices typically have a very small bore size, are designed to cut or "punch" through epidermis, dermis and subdermis layers, do not have a convenient means of restricting the depth of the incision, and are not designed to provide an optimal cosmetic result. In contrast, the cutting devices disclosed herein are designed for cutting much larger circular areas. They can provide the ability to cut to a specific depth (allowing, e.g., cutting only the epidermis without cutting the underlying tissue layers, thereby preserving the blood supply), and can provide an optimal cosmetic result.

Figure 5:
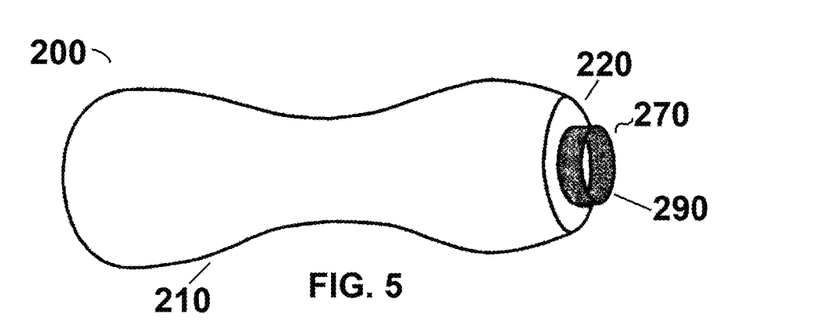
FIG. 5: A partial-side and end view of the surgical cutting device 200 with a circular scalpel 280 as the cutting implement 270 on end 220.

The cutting implement 270 preferably comprises means adapted for making a surgical incision, particularly a circular incision. In presently preferred embodiments, a circular scalpel 290 is used, e.g. as depicted in the embodiment shown in FIGS. 5 and 6. It is contemplated that other means such as electrosurgical devices, lasers, electronic scalpels, ultrasonic cutting implements, microplasma cutters, or the like, may also be used.

In a preferred embodiment the cutting implement 270 extends or protrudes sufficiently from the end 220 of the device body to allow a circular incision to be made around a raised area on the subject, without substantial contact, particularly interfering contact, between the device body 210 and the surgical patient, except as described below.

Not withstanding the foregoing, contact between the device body 210 and the surgical patient's body may be used to control or restrict the depth of the incision. The cutting device 200 may be designed such that the cutting implement 270 protrudes from the end 220 of the device body 210 only to the extent required to make an incision of the desired depth. In one embodiment the cutting implement 270 protrudes from the end 220 of the device body 210 only enough for the incision to penetrate the outer skin layer(s) (i.e. epidermis). When the surgeon applies pressure to the cutting device 200 the circular scalpel 290 penetrates (i.e. cut) the surgical patient's skin to a predetermined depth (e.g. 2 mm) thereafter, the end 220 of the device body 210 makes contact with the surgical patient's body indicating to the surgeon that the incision is of the desired depth.

Figure 6:
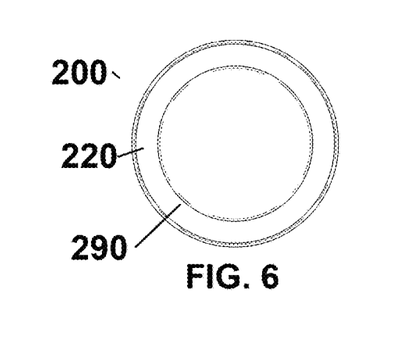
FIG. 6: A profile view of the end 220 of device 200 showing the circular scalpel 290.

In one embodiment, the cutting implement 270 extends about 1-3 mm from the device body 210. More particularly, in such embodiments the circular scalpel 290 is preferably adapted to make an incision the depth of which is limited when the end 220 of the device body 210 makes contact with the surgical patient. Preferably the depth of the incision in some embodiments is limited to about 2 mm or the thickness of the epidermis of a human generally.

Alternatively, other means for limiting or controlling the depth of the incision are contemplated for use herein. For example the depth of the incision may be controlled by a mechanism that increases or decreases the extension of the cutting implement and or scalpel. Such mechanisms can be based on the raised area is a nipple in a preferred embodiment, but may be any raised area including for example a mole, cancerous tissue, skin condition, or infected area.

In one embodiment, as depicted in FIG. 9, the device comprises an incision depth stop 275, which limits the depth of the surgical incision by contacting the patient's body to let the surgeon know the incision is complete. In the absence of such depth stop 275, it is possible for the surgeon to cut too deeply with the circular scapel 290. In certain embodiments, the incision depth stop 275 restricts the incision depth to from about 1 mm to about 1 cm. In other embodiments, the depth of the incision is from about 1 mm to about 5 mm, or from about about 1.5 to 3 mm. In certain embodiments, the depth of the incision is based on cutting a predetermined number (e.g. one or more layers) of the patient's dermis. In one embodiment, as shown in FIG. 9, the incision depth stop 275 is affixed to the body or handle, and is set for one fixed depth. The depth stop 275 may be manufactured as a contiguous part of the handle or body, or may be attached thereto as a separate part. In one embodiment, the depth stop 275 is adjustable (not shown).

The cutting implement 270 extends or protrudes less than about 1 cm from the device body 210 in certain embodiments. In one embodiment, the cutting implement 270 and any cutting blade 290 are recessed while not in use via a retractor and can be extended by releasing the retractor (not shown). In another embodiment, a protective cover (not shown) is used on the end 220 to keep the blade 290 from causing any unintended cuts or harm.

The surgical cutting device 200 can be resterilized and reused in various embodiments, while in other embodiments the device 200 is a single-use item. Other options are also useful, for example, the device body 210 may be reusable but the cutting implement is a single-use item that is disposable or recyclable.

The diameter of the circular scalpel 290 is generally selected based on the diameter of a circular incision required in a surgical procedure. The device 200 is well adapted for uses where the surgical procedure is a breast surgery and the diameter is the desired diameter of a nipple portion of the breast.

In various embodiments, the cutting implement 270 can be removably attached to the end of the body 210. For example, the cutting implement can be snap-fit or twist fit into the end of the body allowing the surgeon to select an appropriate or desired size for the incision.

The surgical cutting device 200 can further comprise a marking implement adapted for making a circular incision on the subject, such as those described with respect to the first aspect of this disclosure. The marking implement (not shown) is affixed to the second end 222 of the body 210 and extends or protrudes sufficiently from the end 222 of the device body 210 to allow making a temporary circular mark on the subject while avoiding substantial contact between the subject and the device body 210. In such a combined device 200, the surgeon would generally use end 222 and its affixed marker to mark the area to be cut on the patient, and then turn or flip the device 200 end-over-end and employ end 220 and its affixed cutting implement 270 to make the incision of the marked circular area.

In another aspect of the disclosure, provided are combination marking and cutting devices comprising a body having a central handle portion adapted for handling by a surgeon during surgery, and at least first and second ends wherein the first end has affixed thereto a marking implement adapted for making a temporary circular mark on a patient, wherein the marking implement extends or protrudes sufficiently from the first end of the device body to allow the marking of the patient with the marking implement while avoiding substantial contact between the patient and the device body, and wherein the second end has affixed thereto a cutting implement adapted for making a circular incision on a subject, wherein the cutting implement extends or protrudes sufficiently from the end of the device body to allow making a circular incision of the desired depth on the subject while avoiding substantial interfering contact between the subject and the device body, wherein the cutting implement comprises a circular scalpel.

The skilled artisan will appreciate that the disclosures above can apply equally to this marking and cutting device, and that any of the features or methods of making the foregoing devices may be useful with this aspect of the disclosure. The combined marking and cutting device provides the convenience of both helpful features in a single device, however, some surgeons may prefer devices which are more specifically adapted for their own handling. The manipulation, feel, and/or handling of the marking tool/device are generally different from the cutting tool/device. However, it may be considerably less expensive in terms of materials, manufacturing, sterilization, shipping, storage, and inventory requirements to utilize a device providing both functions.

In yet another aspect of the invention, provided herein are methods of performing surgical incisions. The methods generally comprise the steps of:
  a) providing a marking device comprising a body having a central handle portion adapted for handling by a surgeon during surgery, and a marking implement adapted for making a temporary circular mark on a patient, wherein the marking implement is affixed to a first end of the body and extends or protrudes sufficiently from the end of the device body to allow the marking of the patient with the marking implement while avoiding substantial contact between the patient and the device body;
  b) using the marking device for making a circular mark on the patient in at least a first location on the subject where a circular incision is desired;
  c) providing a surgical cutting device comprising a body having a central handle portion adapted for handling by a surgeon during surgery, and a cutting implement adapted for making a circular incision on a subject, wherein the cutting implement is affixed to a first end of the body and extends or protrudes sufficiently from the end of the device body to allow making an incision of the desired depth on the subject while avoiding substantial interfering contact between the subject and the device body, wherein the cutting implement comprises a circular scalpel; and
  d) using the cutting device to make a circular incision on the patient in at least the first location.

Optionally, the method comprises the additional steps of making one or more alignment marks on both an area of tissue that is excised or partially-excised from the patient and on the patient's body where the incision was made; and using the alignment marks to return the excised or partially-excised tissue to its original position in the same area from which it was excised.

In some embodiments, the method includes the steps of marking and making a circular incision at a second location on the subject's body. Subsequent additional marking and/or incision steps may also be included.

With reference to FIG. 7, a representative surgical sequence is shown with steps of a procedure (e.g. a breast lift) during which a nipple is relocated from its original location A to a final location C. The nipple is originally present at it location (A). The nipple area is marked using the marking device and a first incision is made with the surrounding tissue cut to the desired depth. Undesired, excess, or stretched skin (shown as hatched area) can be fully removed at this stage. The nipple remains attached to the underlying tissues including its original blood supply and innervation. The nipple can be suppressed while skin from nearby points a and b are brought in adjacent one to the other to close the area where skin was removed. This results in a temporary state where the nipple is beneath the surface. Points a and b may be attached to each other by any suitable means known to surgeons. In the case of a breast lift, suitable suturing such as microsuturing may be useful to provide the best cosmetic results. The displaced nipple is relocated to position C where a second incision is marked and cut to form a hole through which the nipple below may be brought. The now relocated nipple is brought through the hole at location C and sutured into place. Alignment markings present on the nipple and at position C may be present and used to align the nipple so that it is positioned in a similar or identical orientation to that at location A.

The method provides many benefits, including the improved cosmetic possibilities and improved healing for the patient, and ease of use and substantial saving of time for a surgeon having to make one or more nearly perfect surgical incisions. There is also a lowered risk of surgical complications. The methods virtually eliminate the possibility of twisting, e.g. when relocating the subject's nipple.

In another aspect of the invention, kits for marking a circular area on a patient and/or making a circular incision on a patient are provided herein. The kits include
  a) one or more of:
    1) a marking device comprising a body having a central handle portion adapted for handling by a surgeon during surgery, and a marking implement adapted for making a temporary circular mark on a patient, wherein the marking implement is affixed to a first end of the body and extends or protrudes sufficiently from the end of the device body to allow the marking of the patient with the marking implement while avoiding substantial contact between the patient and the device body;
    2) a surgical cutting device comprising a body having a central handle portion adapted for handling by a surgeon during surgery, and a cutting implement adapted for making a circular incision on a subject, wherein the cutting implement is affixed to a first end of the body and extends or protrudes sufficiently from the end of the device body to allow making an incision of the desired depth on the subject while avoiding substantial interfering contact between the subject and the device body, wherein the cutting implement comprises a circular scalpel; and
    3) a combination marking and cutting device comprising a body having a central handle portion adapted for handling by a surgeon during surgery, and at least first and second ends wherein the first end has affixed thereto a marking implement adapted for making a temporary circular mark on a patient, wherein the marking implement extends or protrudes sufficiently from the first end of the device body to allow the marking of the patient with the marking implement while avoiding substantial contact between the patient and the device body, and wherein the second end has affixed thereto a cutting implement adapted for making a circular incision on a subject, wherein the cutting implement extends or protrudes sufficiently from the end of the device body to allow making a circular incision of the desired depth on the subject while avoiding substantial interfering contact between the subject and the device body, wherein the cutting implement comprises a circular scalpel; and
  b) any one or more of instructions for use; written, video, or audio information on using the components of the kit, breast surgery, cosmetic surgery or making circular incisions during surgery, or how a surgeon or hospital can benefit from the kit; information about improving cosmetic results of a breast surgery, a label or other indicia that encourages or promotes use of the devices or the kit for improved cosmetic results in surgeries, or a label or other indicia indicating the devices contained therein are single-use or conditions under which they may be reused; or a link (in the form of a URL) to a website that comprises information on any of the foregoing.

The scope of the invention is set forth in the claims appended hereto, subject, for example, to the limits of language. Although specific terms are employed to describe the invention, those terms are used in a generic and descriptive sense and not for purposes of limitation. Moreover, while certain presently preferred embodiments of the claimed invention have been described herein, those skilled in the art will appreciate that such embodiments are provided by way of example only. In view of the teachings provided herein, certain variations, modifications, and substitutions will occur to those skilled in the art. It is therefore to be understood that the invention may be practiced otherwise than as specifically described, and such ways of practicing the invention are either within the scope of the claims, or equivalent to that which is claimed, and do not depart from the scope and spirit of the invention as claimed.

I claim:

1. A surgical cutting device comprising:
   a body having a first end and a second end;
   a central handle portion located between the first end and the second end, wherein the central handle is manipulated by a surgeon during surgery; and
   a circular cutting implement extending a specific length from the first end of the device body, the specific length of the cutting implement being determined by a predetermined depth of an incision to be made on the patient, wherein the cutting implement makes a uniform circular incision on the patient's breast or around the patient's nipple to the predetermined depth; and
   a depth stop, the depth stop limiting the depth of the incision by contacting the patient's body and notifying the surgeon the incision is complete, wherein the depth stop is set for one fixed depth equivalent to the thickness of the epidermis, wherein the depth stop is affixed to the body on the first end of the device, the depth stop being simultaneously located interior to the cutting implement.

2. The surgical cutting device of claim 1 wherein the cutting implement comprises a fixed circular scalpel shaped in a cylinder with a circle as a base, wherein said scalpel when placed flush on a patient's skin will incise a circle no further than through the patient's epidermis.

3. The surgical cutting device of claim 1 wherein the specific length of the cutting implement extends from the end of the device body to allow the circular incision to be made around a raised area on the patient, wherein the raised area is the nipple.

4. The surgical cutting device of claim 1 wherein the specific length extends or protrudes less than 1 cm from the device body.

5. The surgical cutting device of claim 1 wherein the diameter of the circular cutting implement is determined based on the desired diameter of the nipple portion of the breast.

6. The surgical cutting device of claim 1, wherein the central handle portion is narrower than the first end and the second end of the device body.

* * * * *